United States Patent [19]

Ihara et al.

[11] 4,278,935
[45] Jul. 14, 1981

[54] ELECTRODES FOR MOISTURE METER

[75] Inventors: Susumu Ihara; Kizashi Nakamura, both of Osaka, Japan

[73] Assignee: Sumitomo Electric Industries, Ltd., Osaka, Japan

[21] Appl. No.: 50,219

[22] Filed: Jun. 20, 1979

[30] Foreign Application Priority Data

Jul. 6, 1978 [JP] Japan .............................. 53-93679[U]
Jul. 6, 1978 [JP] Japan .............................. 53-93680[U]
Dec. 8, 1978 [JP] Japan ............................ 53-169542[U]

[51] Int. Cl.³ .............................................. G01R 27/26
[52] U.S. Cl. ................................. 324/61 P; 324/65 P
[58] Field of Search ................... 324/61 P, 61 R, 65 P; 361/280, 281, 284, 285, 286

[56] References Cited

U.S. PATENT DOCUMENTS 2,692,972  10/1954  Edgerton et al. .................. 324/61 P

FOREIGN PATENT DOCUMENTS 1317573  1/1963  France .................................... 324/61 P
195059   3/1965  Sweden ................................... 324/61 P
709177   5/1954  United Kingdom ................... 324/61 P Primary Examiner—Ernest F. Karlsen
Attorney, Agent, or Firm—Wenderoth, Lind & Ponack

[57] ABSTRACT

An improved electrode assembly for an electrostatic type moisture meter for powdery or granular material includes an insulator, a high-tension electrode in the form of a stick mounted on the insulator so as to vertically extend therefrom, and a plurality of earth electrodes in the form of sticks arranged around and in parallel with the high-tension electrodes. The high-tension electrode has a protection insulator at the tip thereof. The insulator has air-emitting openings for emitting air therefrom to the base portion of the electrodes to remove the material remaining at the base portion of the electrodes after a measurement. The insulator preferably has an outer face sloped at its periphery.

9 Claims, 11 Drawing Figures

ELECTRODES FOR MOISTURE METER

BACKGROUND OF THE INVENTION

The present invention relates to an electrode assembly for an electrostatic moisture meter for powdery or granular material.

Various methods have been proposed for taking measurement of the water content of powdery or granular material, among which is an electrostatic method. In this method, the electrostatic capacity between a high-tension electrode and an earth electrode with a powdery material therebetween is measured. The thus obtained capacity measurement is in turn converted into a measurement of the water content in accordance with the proportionality of the capacity of the material to the water content thereof.

A conventional electrode assembly is shown in FIG. 1. The assembly includes a cylindrical insulator 3 of Bakelite, for example, a high-tension electrode 1, earth electrodes 2 both secured on the inner face of the insulator, and a guard electrode 4' on the outer face of the insulator. This electrode assembly, however, has some disadvantages. One of the most important disadvantages is related to the shape of the assembly. As is apparent, it is not easy to insert the electrode assembly into a powdery material under measurement since the assembly has a cylindrical form. Upon insertion, the electrode assembly may cause a change of the state of the material and make an unstable contact therewith to provide an inaccurate measurement since the electrodes involved have a large surface area. A further disadvantage in the prior electrode assembly is that it has a large stray capacity which also makes an accurate measurement of the capacity of the material difficult.

SUMMARY OF THE INVENTION

The present invention has been accomplished to obviate the disadvantages as above mentioned, and to provide an improved measuring electrode assembly for an electrostatic moisture meter which includes such electrodes as can be readily inserted into a powdery or granular material to make a stable contact therewith, and also to minimize the effect of the stray capacity involved, thereby permitting an accurate measurement of the capacity of the material between the electrodes.

According to the present invention, there is provided an improved measuring electrode assembly which includes at least one high-tension electrode in the form of a stick or rod and a plurality of earth electrodes in the form of sticks or rods arranged around and in parallel with the high-tension electrode.

The improved electrode assembly, however, still has some problems to be settled. After the electrodes have been drawn out of the powdery material under measurement, the material such as sand may still remain at the base portion of the electrodes, that is, a portion where the electrodes are fixed onto the insulator. The thus remaining material may form a bridge between the electrodes. This may provide an incorrect measurement of the electrostatic capacity in subsequent measurements due to an incorrect drift compensation.

In the improved electrode assembly, the electrodes have conical tips so that they can be readily inserted into the powdery material. Thus, the electrodes, when of stainless steel or copper as usual, will wear after repeated measurements, to provide an error in measurement due to the change in length of the electrodes.

A further problem is that when the electrodes are inserted into the material to the direction shown by the arrow a as is shown in FIG. 2a, the material under the insulator may move or escape in the directions shown by the arrows b since the insulator has a smooth outer face. Accordingly the material may not be pressed under a uniform pressure.

It is, therefore, an object of the present invention to provide an improved measuring electrode assembly for an electrostatic moisture meter which includes electrodes readily inserted into a powdery or granular material under measurement to make a stable contact therewith and to minimize the effect of the stray capacity involved, thereby permitting an accurate measurement of the electrostatic capacity of the material between the electrodes.

It is also an object of the invention to provide an electrode assembly for an electrostatic moisture meter so adapted that the material will not remain at the base portion of the electrodes after they are drawn out of the material.

It is a further object of the present invention to provide an electrode assembly for an electrostatic moisture meter which includes a high-tension electrode prevented from wearing.

It is still an object of the invention to provide an electrode assembly for an electrostatic moisture meter which permits the measurement of the capacitance of the material under a uniform pressure applied thereto.

BRIEF DESCRIPTION OF THE DRAWINGS

Other objects and features of the invention will be apparent from the following description taken with reference to the accompanying drawings, in which.

DETAILED DESCRIPTION OF THE INVENTION

Like numerals are employed to designate like or corresponding parts or elements throughout the drawings.

Figure 2A:
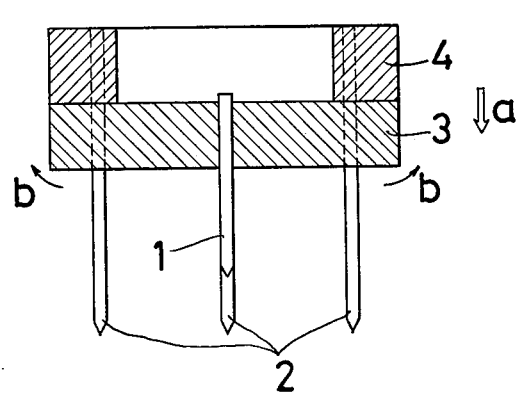
FIG. 2a is a vertical sectional view of a first embodiment of a measuring electrode assembly for an electrostatic moisture meter according to the present invention.
Figure 2B:
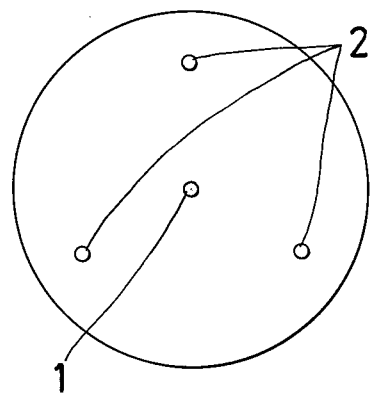
FIG. 2b is a plan view thereof.

Referring now to FIGS. 2a and 2b illustrating a first embodiment of the electrode assembly of the invention, it includes an insulator 3, a high-tension electrode 1 in the form of a stick or rod secured at the center of the outer face of the insulator so as to vertically extend therefrom, and three earth electrodes 2 in the form of sticks or rods arranged in an angularly equally spaced relation around and in parallel with the high-tension electrode. All the electrodes 1 and 2 have conical tips so that they can be readily inserted into a powdery or granular material. The earth electrodes are fixed by an annular member 4, and made longer than the high-tension electrodes to minimize the effect of stray capacity.

During measurement, the electrodes only are inserted into the material. This is in contrast with the case of the prior assembly wherein the entire assembly has to be inserted into the material.

Figure 3A:
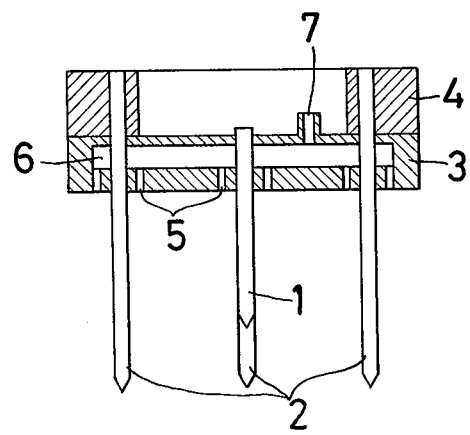
FIG. 3a is a vertical sectional view of a second embodiment according to the invention.
Figure 3B:
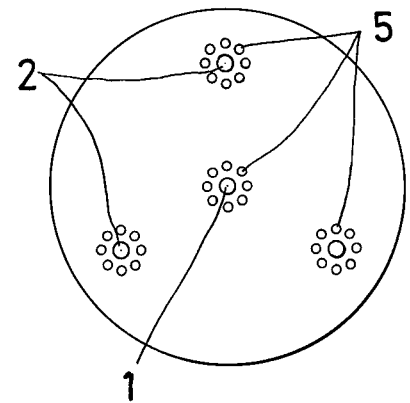
FIG. 3b is a plan view thereof.

FIGS. 3a and 3b illustrate a second embodiment of the electrode assembly of the invention. This assembly, similar to that of FIGS. 2a and 2b includes an insulator 3, a high-tension electrode 1, and three earth electrodes, all mounted on the insulator. The insulator, however, has an air-supply opening 7 on the inner face thereof so as to communicate with a hollow 6 within the insulator, and air-emitting openings 5 communicating with the hollow and extending to the outer face of the insulator around the electrodes in the neighborhood thereof, so that air can be emitted therefrom over the base portion of the electrodes after the electrodes are drawn out of the material.

This embodiment prevents the powdery material from remaining on the base portions of the electrodes after measurement, and thus prevents potential error in subsequent measurement due to incorrect drift compensation.

Figure 1:
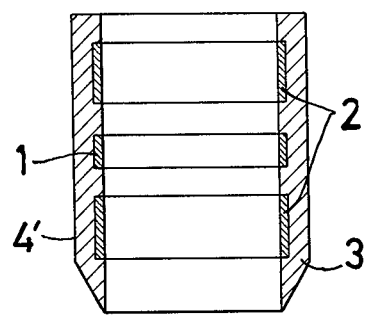
FIG. 1 is a vertical sectional view of a conventional electrode assembly for an electrostatic moisture meter.
Figure 4:
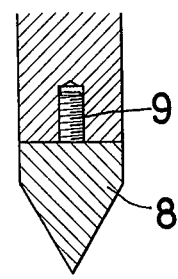
FIG. 4 is an enlarged vertical sectional view of the top of a high-tension electrode preferably used in the invention.

According to the invention, as is shown in FIG. 4, the high-tension electrode 1 preferably has a protection insulator 8 of ceramic or the like at the tip thereof so as to prevent the wearing of the top of the electrode. The insulator may be made of cemented carbide. The protection insulator may be fixed onto the tip of the electrode either by an adhesive or a screw 9 as is shown. In this embodiment, too, the earth electrodes are longer than the high-tension electrode.

This embodiment permits a stable and accurate measurement of the capacity of the material since there occurs no wearing of the tip of the high-tension electrode.

Figure 5A:
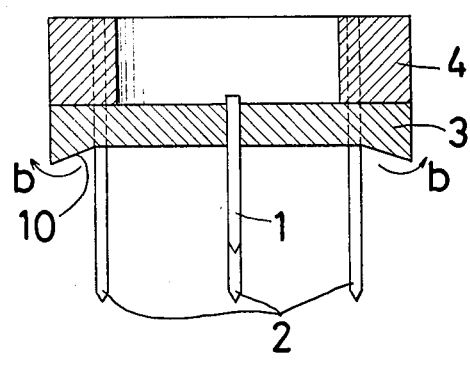
FIG. 5a is a vertical sectional view of a third embodiment according to the invention.
Figure 5B:
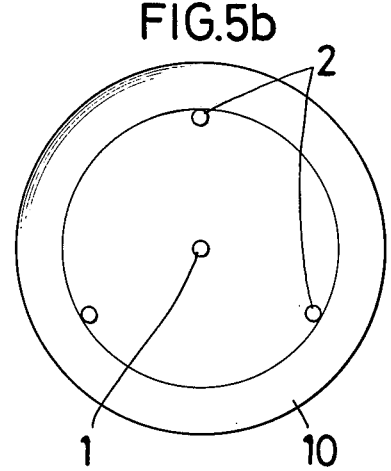
FIG. 5b is a plan view thereof.

FIGS. 5a and 5b illustrate a third embodiment of the electrode assembly of the invention. The assembly includes an insulator 3 having at the outer face thereof an annular slope 10 inwardly inclining to form a dent or recess at the central portion of the insulator. The slope prevents the material under the insulator from escaping in the directions shown by the arrows b when the electrodes are inserted into the material, thereby ensuring the measurement of the capacity of the material under a uniform pressure applied thereto.

Figure 6:
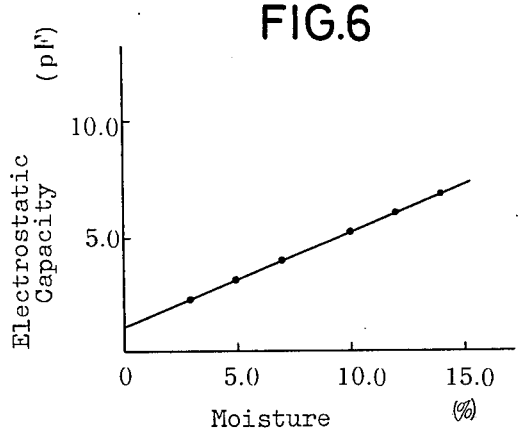
FIG. 6 is a graph illustrating the proportionality of the electrostatic capacity of sand to the water content thereof.

FIG. 6 illustrates the linear relationship between the electrostatic capacity of the sample material and the water content thereof when using the improved electrode assemblies of the invention as has been described above. A high reproductivity is also realized.

Figure 7:
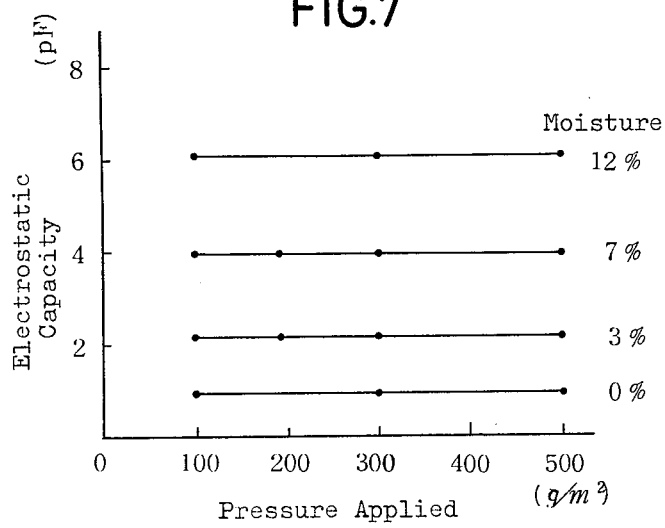
FIG. 7 is a graph illustrating the relationship between the pressure applied to sand and the capacity thereof measured under the pressure.

FIG. 7 illustrates the relationship between the measured capacities of material of different water contents and the pressure applied to the material. As is apparent, the pressure applied to the material has no effect upon the measurement. (The measurement was made by the use of apparatus disclosed in Japanese Patent Application No. 51-72064.)

Figure 8:
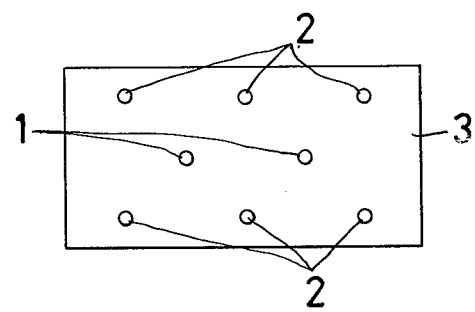
FIG. 8 is a plan view of a fourth embodiment according to the invention.

FIG. 8 illustrates still a further embodiment of the electrode assembly according to the invention, in which two high-tension electrodes 1 are mounted in a line on an insulator 3, and a plurality of earth electrodes 2 are arranged in two lines and in parallel with the high-tension electrodes. This type of assembly is in particular suitable for taking measurements of a wide range of moisture. In this embodiment, too, the earth electrodes are made longer than the high-tension electrodes to minimize the effect of the stray capacity involved.

It will be understood that although this invention has been described with reference to preferred embodiments, various changes or variations may be made within the scope of the present invention.

What are claimed are:

1. An electrode assembly for an electrostatic moisture meter of the electrostatic capacity type for determining the moisture content of powdery or granular material, said assembly comprising:
    an insulator;
    at least one high-tension electrode in the form of a rod mounted in said insulator and extending outwardly therefrom; and
    a plurality of earth electrodes in the form of rods, said earth electrodes being mounted in said insulator at locations spaced around said high-tension electrode, said earth electrodes extending outwardly from said insulator in directions parallel to said high-tension electrode, and said earth electrodes being longer than said high-tension electrode.

2. An assembly as claimed in claim 1, wherein all of said electrodes are fixedly mounted in said insulator.

3. An assembly as claimed in claim 1, wherein the tip of the outer end of said high-tension electrode includes a protector formed of ceramic or cemented carbide.

4. An assembly as claimed in claim 1, wherein the tips of the outer ends of said electrodes are conically pointed.

5. An assembly as claimed in claim 1, comprising a plurality of said high-tension electrodes mounted in said insulator in a row, and wherein said plurality of earth electrodes are arranged in rows on opposite sides of said row of high-tension electrodes and extending parallel thereto.

6. An assembly as claimed in claim 1, wherein said insulator includes means for emitting air therefrom to blow said air against the base portions of each of said electrodes, and for thereby removing granular or powdery material retained on said electrodes after the removal thereof from material which has been measured.

7. An assembly as claimed in claim 6, wherein said emitting means comprises a hollow space within said insulator, an air supply opening extending into said hollow space, and air-emitting openings extending through said insulator from said hollow space to positions adjacent said base portions of said electrodes.

8. An assembly as claimed in claim 1, wherein said insulator includes means for, upon the insertion of said electrodes into granular or powdery material, preventing the material positioned beneath the insulator from moving in directions laterally from beneath said insulator, said preventing means comprising a flange extending outwardly from the entire periphery of said insulator.

9. An assembly as claimed in claim 8, wherein said flange has an inner peripheral surface inclined outwardly from said insulator, thereby defining in said insulator a recess surrounded by said flange.

* * * * *